(12) United States Patent
Cho et al.

(10) Patent No.: US 8,871,958 B2
(45) Date of Patent: Oct. 28, 2014

(54) METHOD FOR PREPARING 5-CHLOROMETHYL-2-FURFURAL USING GALACTAN DERIVED FROM SEAWEED IN TWO COMPONENT PHASE

(75) Inventors: Jin-Ku Cho, Yongin-si (KR); Sang-Yong Kim, Yongin-si (KR); Do-Hoon Lee, Seoul (KR); Bo Ra Kim, Daejeon (KR); Jae-Won Jung, Seoul (KR)

(73) Assignee: Korea Institute of Industrial Technology (KR)

( * ) Notice: Subject to any disclaimer, the term of this patent is extended or adjusted under 35 U.S.C. 154(b) by 0 days.

(21) Appl. No.: 13/985,019

(22) PCT Filed: Feb. 16, 2012

(86) PCT No.: PCT/KR2012/001171
§ 371 (c)(1),
(2), (4) Date: Nov. 14, 2013

(87) PCT Pub. No.: WO2012/111988
PCT Pub. Date: Aug. 23, 2012

(65) Prior Publication Data
US 2014/0066641 A1    Mar. 6, 2014

(30) Foreign Application Priority Data
Feb. 16, 2011  (KR) .......... 10-2011-0013826

(51) Int. Cl.
*C07D 307/46* (2006.01)
*B01J 31/02* (2006.01)

(52) U.S. Cl.
CPC ........... *C07D 307/46* (2013.01); *B01J 31/0231* (2013.01)
USPC ........................................ 549/498

(58) Field of Classification Search
USPC ........................................ 549/498; 502/150
See application file for complete search history.

(56) References Cited

U.S. PATENT DOCUMENTS

| 4,154,744 | A | 5/1979 | Hamada et al. |
|---|---|---|---|
| 4,335,049 | A | 6/1982 | Hamada et al. |
| 4,424,390 | A | 1/1984 | Hamada et al. |
| 7,829,732 | B2 | 11/2010 | Mascal et al. |
| 2009/0234142 | A1 | 9/2009 | Mascal |
| 2010/0267708 | A1* | 10/2010 | Kim et al. .................. 514/228.2 |

OTHER PUBLICATIONS

Mark Mascal and Edward B. Nikitin, Dramatic Advancements in the Saccharide to 5-(Chloromethyl) furfural Conversion Reaction. 2009, 3 pages, 2009 Wiley-VCH Verlag Gmbh & Co. KGaA, Weinheim.
PCT/KR2012/001171 International Search Report, Feb. 7, 2012.
Patent Gazette, 2 pages, Aug. 31, 2012.

* cited by examiner

*Primary Examiner* — Kristin Vajda
(74) *Attorney, Agent, or Firm* — Hahn Loeser & Parks LLP

(57) ABSTRACT

The present disclosure relates to an acid catalyst composition for producing 5-chloromethyl-2-furfural from galactan derived from seaweed and a method for producing 5-chloromethyl-2-furfural from galactan derived from seaweed on a two component phase using the acid catalyst, the acid catalyst composition for producing 5-chloromethyl-2-furfural from galactan derived from seaweed including organic solvent and dilute hydrochloric acid, a concentration of the dilute hydrochloric acid being 4N to 8N (normal).

According to the present disclosure, there is an advantage of converting 5-chloromethyl-2-furfural from galactan derived from seaweed by means of a single process by mixing dilute hydrochloric acid and organic solvent by an optimal ratio, unlike conventional methods for producing 5-chloromethyl-2-furfural that had to go through a multi-phase process of preconditioning and saccharification.

14 Claims, 3 Drawing Sheets

METHOD FOR PREPARING 5-CHLOROMETHYL-2-FURFURAL USING GALACTAN DERIVED FROM SEAWEED IN TWO COMPONENT PHASE

CROSS REFERENCE TO RELATED APPLICATIONS

This application is a national stage application of PCT/KR2012/001171 filed on Feb. 16, 2012, which claims priority to Korean Application No. 10-2011-0013826 filed Feb. 16, 2011 the disclosure of which is incorporated by reference herein.

BACKGROUND

1. Field

The following description relates to an acid catalyst composition for preparing 5-chloromethyl-2-furfural from galactan derived from seaweed, and a method for preparing 5-chloromethyl-2-furfural from galactan derived from seaweed in a two-component phase using the acid catalyst composition, and more particularly, to an acid catalyst composition for preparing 5-chloromethyl-2-furfural from galactan derived from seaweed capable of preparing 5-chloromethyl-2-furfural in a single process by using dilute hydrochloric acid and organic solvent under an optimal reaction condition, thereby significantly saving the processing costs, and a method for preparing 5-chloromethyl-2-furfural from galactan derived from seaweed in a two-component phase using the acid catalyst composition.

2. Description of Related Art

Currently, oil resources prices are rapidly rising due to increase of demand caused by limited oil reserves and emergence of new developing countries including China, and depletion of oil resources is expected to become a reality in the near future. Oil is nonrenewable resource for which massive environmental costs are expected due to international agreements, and thus numerous countries are making much effort to replace oil resources.

The most practical alternative to such irreversible fossil resource is to use renewable and sustainable carbohydrate biomass. Already many countries that have vast arable land such as the United States and Brazil etc. started to industrially mass produce bio-ethanol from starting materials of sugar from sugar cane and starch from corn through saccharification and fermentation processes.

Carbohydrate biomass may be classified into crop-line carbohydrate biomass and wood-line carbohydrate biomass, and carbon source that may be obtained from such carbohydrate biomass includes starch or sugar that may be obtained from crop-line biomass and cellulose that may be obtained from wood-line carbohydrate biomass. These polysaccharide materials are obtained through a pre-conditioning process of biomass resources, and the polysaccharide materials of starch, sugar, and cellulose obtained through the pre-conditioning process change into glucose or fructose that are hexose through a monosaccharide process by hydrolysis, and then change into alternatives to petroleum or chemical products through biological fermentation or chemical catalyst processes.

More specifically, a general method for obtaining a final compound from carbohydrate biomass source of supply requires multi-phase processes of (a) a pre-conditioning process for obtaining starch, sugar, and cellulose which are polysaccharide materials from raw materials, (b) a monosaccharide process for obtaining glucose and fructose, and (c) biological fermentation or catalyst chemical process for obtaining a final compound, and there is a problem that the yield rate is reduced in the process of going through such a multi-phase process.

In addition, crop-line biomass source of supply utilizes food resources and thus causes international crop prices to rise due to the problem of sharing food resources and arable land, and since the cultivating cost is pegged to oil prices, it is highly controversial internationally.

In order to solve the aforementioned problem, wood-line biomass source is drawing much attention due to the fact that wood may be supplied in large volumes since wood grows autonomously and does not share arable land with agricultural produce, and urban waste wood or forest by-products scattered in many forests may be utilized as raw material. However, in case of such wood-line biomass, it is difficult to effectively separate and remove solid lignin that accounts for approximately 30% of the total components in the preconditioning process, and much research is needed regarding utilization of discarded lignin. Moreover, cellulose which is the starting material of wood-line biomass is chemicophysically more stable compared to sugar or starch which is the starting material of crop-line biomass, and thus there is a problem of having a high degree of difficulty in the conversion process.

To solve the aforementioned problems, marine resources have attracted attention as a third-generation biomass. Marine resources have large cultivation areas, and there is almost no cost increase caused by the use of freshwater, land, and fertilizer, and there is excellent growth potential, and thus have great production per unit area. hus, developing conversion technologies that could produce alternative fuels and compounds utilizing marine biomass resources as a new source of supply is expected to have important implications for the post-oil era.

It has been reported that agarose, which is the main ingredient of giant algae as a marine-line biomass resource has different chemical structural features than the cellulose in ground plants, and thus chemical conversion is easy.

In addition, there are conventional methods for producing 5-chloromethylfurfural using cellulose, which costs a lot of money in conversion reactions, harmful to the human bodies, and requires using thick hydrochloric acid under pressurized conditions, and thus are very dangerous processes that require equipments that could withstand the strong acid.

Thus, it is desirable to develop a method for producing pure 5-chloromethyl-2-furfural from galactan derived from seaweed more easily and under milder conditions than conventional methods, and without going through complicated pre-conditioning and saccharification processes that cost a lot of money.

SUMMARY

The present disclosure is for resolving the aforementioned problems, and the purpose of the present disclosure is to provide an acid catalyst composition for producing 5-chloromethyl-2-furfural from galactan derived from seaweed that may convert galactan derived from seaweed into 5-chloromethyl-2-furfural in a simple single process by mixing dilute hydrochloric acid and organic solvent by an optimal ratio, unlike the conventional methods for producing 5-chloromethyl-2-furfural which had to go through a multi-phase process including a preconditioning and saccharification process, and a method for producing 5-chloromethyl-2-furfural from galactan derived from seaweed on a two component phase using the acid catalyst.

In addition, the purpose of the present disclosure is to extract carbohydrate that has high content of carbohydrate more easily than conventional methods with significantly reduced raw material costs, causing no problems to crop prices, by having galactan derived from seaweed that doesn't cause food problems as the raw material.

Not only that, the purpose of the present disclosure is to provide an acid catalyst composition for producing 5-chloromethyl-2-furfural from galactan derived seaweed where conversion reaction is possible with only acid catalyst and not metal catalyst under more mild conditions, and a method for producing 5-chloromethyl-2-furfural from galactan derived seaweed in a two component phase using the acid catalyst.

In addition, the purpose of the present disclosure is to prevent generation of waste acid and waste water from preconditioning and saccharification, reduce energy consumption significantly, and by using dilute hydrochloric acid, reducing risk during the process, and improving environment-friendliness.

In one aspect of the present disclosure, an acid catalyst composition for producing 5-chloromethyl-2-furfural from galactan derived from seaweed is characterized to include an organic solvent and dilute hydrochloric acid, wherein a concentration of the dilute hydrochloric acid may be 4N to 8N (normal).

The dilute hydrochloric acid may be 30 to 200 parts by weight of 100 parts by weight of the organic solvent, wherein the organic solvent is halogenated hydrocarbon solvent.

In addition, the halogenated hydrocarbon solvent may be at least one of dichloromethane, chloroform, 1,2-dichloroethane or 1,1,2-trichloroethane.

Furthermore, 10 g to 300 g of galactan may be included in 1 L of dilute hydrochloric acid, and the galactan is agarose.

Next, in one aspect of the present disclosure, a method for producing 5-chloromethyl-2-furfural from galactan derived from seaweed in two component phase includes mixing the galactan, a first organic solvent, and dilute hydrochloric acid to produce a mixture; and reacting by heating and reacting the mixture to produce a reactant.

Herein, the method may further include adding distilled water and a second organic solvent to the reactant; separating the first organic solvent from the reactant by removing the first organic solvent from the reactant in distillation under reduced pressure method; dissolving dichloromethane in the reactant by adding dichloromethane to the reactant; filtering the reactant through silica and activated carbon; and purifying the reactant by removing the dichloromethane from the reactant in distillation under reduced pressure method to produce purified 5-chloromethyl-2-furfural.

In the mixing, the dilute hydrochloric acid may be 30 to 200 parts by weight of 100 parts by weight of the first organic solvent, the first organic solvent is halogenated hydrocarbon solvent, and the halogenated hydrocarbon solvent is at least one of dichloromethane, chloroform, 1,2-dichloroethane, and 1,1,2-trichloroethane.

In addition, in the mixing, the galactan may be 10 g to 300 g in 1 L of dilute hydrochloric acid, and in the reacting, the reacting temperature may be 50 to 200° C.

In the reacting, the reaction is made as the mixture may be stirred, the stirring speed being 100 to 400 RPM, and in the adding, the second organic solvent may be 80 to 120 parts by weight, and the distilled water may be 60 to 150 parts by weight of 100 parts by weight of the first organic solvent.

In the adding, the reactant is separated into a dilute hydrochloric acid layer and an organic solvent layer after the distilled water and the first organic solvent are added, and in the dissolving, 150 to 250 parts by weight of dichloromethane may be added to 100 parts by weight of the first organic solvent.

In addition, in the filtering, the filtering time may be 4 to 8 hours.

According to the present disclosure, there is an advantage that it is possible to convert galactan derived from seaweed into 5-chloromethyl-2-furfural in a single process by mixing dilute hydrochloric acid and organic solvent in an optimal ratio.

In addition, there is an advantage that it is possible to extract carbohydrate having high content of carbohydrate more easily compared to wood-line biomass resources by using galactan derived from seaweed which does not cause food problems as the raw material, thereby significantly reducing raw material costs without affecting the crop prices.

Not only that, unlike the conventional methods, there is an advantage that a conversion reaction is possible with only acid catalyst and without any metal catalyst, under milder conditions thereby increasing the efficiency.

In addition, there is an advantage that it is possible to prevent generation of waste acid and waste water during the preconditioning and saccharification process etc., significantly reduce energy consumption, and by using dilute hydrochloric acid, reduce risk factors and increase environmentally friendliness.

DETAILED DESCRIPTION

Figure 1:
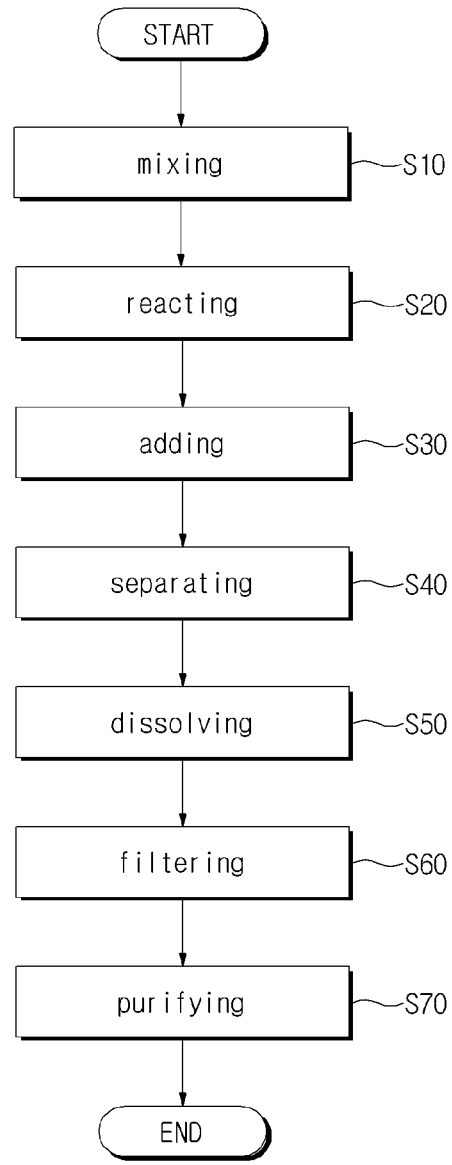
FIG. 1 is a flowchart sequentially illustrating the method for producing 5-chloromethyl-2-furfural from galactan derived from seaweed on a two component phase according to the present disclosure.

Hereinbelow, an acid catalyst composition for producing 5-chloromethyl-2-furfural from galactan derived from seaweed and a method for producing 5-chloromethyl-2-furfural from galactan derived from seaweed on a two component phase using the acid catalyst according a preferred exemplary embodiment is explained in detail with reference to the attached drawings. The exemplary embodiment is for exemplary purpose and not for limiting the scope of protection of the claims.

First of all, the acid catalyst composition for producing 5-chloromethyl-2-furfural from galactan derived from seaweed is formed to include organic solvent and dilute hydrochloric acid, the concentration of the dilute hydrochloric acid being 4N to 8N (normal).

Herein, the organic solvent and the dilute hydrochloric acid play the role of removing a final product produced by a conversion reaction on a two component phase from the dilute hydrochloric acid layer to the organic solvent layer, thereby sustaining the direction of producing 5-chloromethyl-2-furfural by the Le Chatelier's Principle.

That is, as the organic solvent and dilute hydrochloric acid are added to galactan by an optimal volume, a conversion reaction occurs, and through this conversion reaction, 5-chloromethyl-2-furfural is directly produced.

In addition, the concentration of the dilute hydrochloric acid may be preferably 4N to 8N, more preferably 5N to 7N, and most preferably 6N. When the concentration is less than 4N, the conversion reaction does not occur sufficiently and thus reduces the yield, and when the concentration exceeds 8N, high content of hydrochloric acid increases risk factors, decreases environmentally friendliness, and it is uneconomical since equipments that could withstand strong acid would be needed.

In addition, regarding the content ratio of the dilute hydrochloric acid and the organic solvent, it is preferable that the dilute hydrochloric acid may be 30 to 200 parts by weight, and more preferably 60 to 100 parts by weight to 100 parts by weight of the organic solvent. When the dilute hydrochloric acid is either less than 30 parts by weight or above 200 parts by weight, the two component phase conversion reaction cannot be made effectively, thereby significantly reducing the overall yield.

Numerous times of experiments showed that the above content ranges resulted in the most excellent yields.

Preferably, the organic solvent may be halogenated hydrocarbon solvent, more preferably, at least one of dichloromethane, chloroform, 1,2-dichloroethane or 1,2-trichloroethane. It has been confirmed through numerous experiments that the above organic solvent is the optimized material for maximizing the conversion reaction and the yield.

In addition, preferably, the galactan may be 10 g to 300, more preferably 100 g to 200 g in 1 L of dilute hydrochloric acid. This is a limitation to the content ratio of the dilute hydrochloric acid and galactan, and the content ratio outside the above range would reduce the conversion ratio, and reduce the overall yield.

The galactan includes agarose, and the chemical structure of agarose is as in chemical formula I below:

[Chemical formula I]

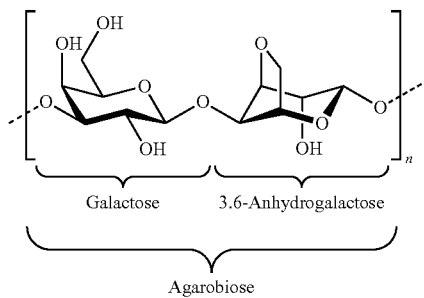

More specifically, agarose is a linear high molecular polymer having Agarobiose as its unit molecule which is a disaccharide molecule consisting of Galactose and 3,6-Anhydrogalactose.

The seaweed used in the present invention is preferably giant seaweed, and any seaweed may be used as long as it includes galactan.

Examples of the seaweed include agar-agar weed, layer, cottoni, *Pachymeniopsis lanceolata, Porphyra Suborbiculata* Kjellman, *Pterocladiella capillacea, Arcanthopeltis japonica, Gloiopeltis tenex* (Turner) J. Agardh, *Gracilaria verrucosa, Chondrus ocellatis* Holmes, *Grateloupia elliptica* Holmes, *Hypnea charoides, Ceramium kondoi, Ceramium boydenii* Gepp, *Chondracanthus tenellus, campylaephora hypnaeoides,* and *Grateloupia filicina.*

Methods for extracting galactan from the above-mentioned seaweed may be any method used in the related field, but in the present disclosure, the most effective method is to immerse the seaweed in an alkali solution for a certain time, then wash the seaweed, and then immerse the washed seaweed in an extract solvent consisting of one of $H_2SO_4$, HCl, HBr, $HNO_3$, $CH_3COOH$, HCOOH, $HClO_4$ (perchloric acid), $H_3PO_4$, PTSA (para-toluene sulfonic acid) for a certain time to extract agar, carrageenan, and alginic acid component.

In addition, in terms of chemical composition, the amount of galactan that could be obtained from giant seaweed in a simple preconditioning process is known to be about 50 to 60% of the total components in the case of red algae such as *Gelidium, Gracilaria*, and the remaining major configurative elements include about 10 to 20% of glucan which is cellulose fiber, 10 to 20% of protein, and 5 to 15% of lipid and ash, but these can be easily removed in the extracting process etc.

As such, unlike crystalline cellulose formed through intramolecular hydrogen bonding and thus has a very low solubility, galactan such as agarose etc. is a high molecular material having excellent solubility in polar solvents. Specifically, agar may be dissolved in hydrophilic organic solvents such as water or alcohol heated to about 80° C. These solubility characteristics are required elements for efficient chemical conversion reactions in the present invention and thus have very important meaning.

That is, the acid catalyst composition for producing 5-chloromethyl-2-furfural from galactan derived from seaweed of the present disclosure has been configured to most efficiently perform the reaction of directly converting 5-chloromethyl-2-furfural from galactan derived from seaweed through numerous experiments.

Next, as illustrated in FIG. 1, a method of producing 5-chloromethyl-2-furfural from galactan derived from seaweed on a two component phase according to the present disclosure includes mixing (S10), reacting (S20), adding (S30), separating or removing (S40), dissolving (S50), filtering (S60) and purifying (S70).

Herein, the mixing (S10) is a step of mixing the galactan, a first organic solvent and dilute hydrochloric acid to produce a mixture. This is a process of effectively mixing the first organic solvent and the dilute hydrochloric acid to facilitate reaction.

The mixing (S10) is effective when made through stirring.

In addition, in the mixing (S10), the first organic solvent is halogenated hydrocarbon solvent, and it is preferable that the halogenated hydrocarbon solvent is at least one of dichloromethane, chloroform, 1,2-dichloroethane and 1,1,2-trichloroethane. Details thereof are as mentioned above.

In addition, in the mixing (S10), the dilute hydrochloric acid is preferably 30 to 200 parts by weight, more preferably 60 to 100 parts by weight of the 100 parts by weight of the first organic solvent. Details thereof are as mentioned above.

In addition, in the mixing (S10), the galactan is preferably 10 g to 300 g, and more preferably 100 g to 200 g in 1 L of dilute hydrochloric acid. Details thereof are as mentioned above.

Next, the reacting (S20) is a step of heating and reacting the mixture to produce a reactant. There is a process of producing the final product, 5-chloromethyl-2-furfural by a conversion reaction by an acid catalyst.

It is preferable that in reacting (S20), the mixture is heated and then reacted through stirring.

Herein, it is preferable that the stirring is made using a stirrer, and the stirring speed may be preferably 100 to 400 RPM, more preferably 200 to 300 RPM. When the stirring speed is less than 100 RPM, the stirring is not made sufficiently, and the reaction is not made efficiently either, whereas when the stirring speed is above 400 RPM, it is not economical, and generates too much by-products, thereby reducing the yield.

In addition, it is preferable that the reaction temperature is 50 to 200° C., more preferably 70 to 120° C., and most preferably 100° C. When the reaction temperature is less than 50° C., there is a problem that not enough heat is applied and thus the reaction is not made well, thereby significantly reducing the conversion rate, whereas when the reaction temperature is above 200° C., by-products such as Humin is generated, significantly reducing the yield etc.

In the reacting (S20), the reactant produced after the mixture goes through the reaction is 5-chloromethyl-2-furfural which includes by-products. This may be utilized as it is, but in order to remove impurities and produce purified 5-chloromethyl-2-furfural, the following process is required.

Regarding the conversion reaction mechanism of the present invention, first of all, H+ combines on top of an oxygen atom in an agarose molecule, and then electrons in the agarose molecule move, initiating the reaction. Herein, by movement of the electrons, chemical bonding in the molecule are simultaneously disconnected or regenerated, causing existence of numerous intermediates having balanced relationship in the reaction solution.

As the reaction time passes, the state of balance is broken by a dehydration process, and a conversion is made into a material of furfural type having the most stable chemical structure thermodynamically, and an additional substituting reaction is made by chloride ions existing in the surroundings, generating 5-chloromethyl-2-furfural as the final product.

Such a conversion reaction process is made in the dilute hydrochloric acid layer, and 5-chloromethyl-2-furfural which is the final product moves to the organic solvent layer since it has high hydrophobicity. As such, as the product is removed from the dilute hydrochloric acid layer in real time, the conversion reaction is made sustainably in the direction of generating 5-chloromethyl-2-furfural by the Le Chatelier's Principle.

Agar reacts more sensitively under acid conditions due to 3,6-anhydrous galactose having big ring strains in terms of chemical structure unlike cellulose, and the connection among agarose is made in C1-C3 instead of the general C1-C4 type, and thus there is an advantage that since the chemical structure of the intermediated it expected to be different, the conversion reaction can be made under more mild acid conditions than cellulose which is a wood-line biomass derived starting material.

Next, the adding (S30) is a step of adding distilled water and a second organic solvent in the reactant. This is a process of adding distilled water and a second organic solvent in order to separate and distinguish layers on a two component phase.

In the adding (S30), it is preferable that the second organic solvent is 80 to 120 parts by weight, and the distilled water is 60 to 150 parts by weight, more preferably, the second organic solvent is 95 to 105 parts by weight, and the distilled water is 90 to 110 parts by weight of the 100 parts by weight of the first organic solvent. However, when the ratio is outside the above-mentioned content ratios, the purifying effect and the quality of the final product 5-chloromethyl-2-furfural will deteriorate.

In addition, in the adding (S30), after the distilled water and the first organic solvent are added, the reactant is separated into a dilute hydrochloric acid layer and an organic solvent layer. This is a process to effectively remove the first organic solvent.

It is preferable that temperature of the adding (S30) is 10 to 30° C. This is to cool the temperature at the reacting (S20), thereby ending the reaction and facilitating separation of the final product.

The adding (S30) is performed to remove the first organic solvent, but this may also be utilized as a plural reaction process of adding an organic solvent again into the dilute hydrochloric acid layer and activating an additional conversion reaction.

Next, the separating or removing (S40) is a step of removing the first and the second organic solvent from the reactant in the distillation under reduced pressure method. This is a process for removing the organic solvent layer separated through the adding (S30) without damaging the final product.

In the separating or removing (S40), it is preferable to remove the first and the second organic solvent by distilling the solvent of the organic solvent layer separated by the adding (S30).

In addition, the dissolving (S50) is a step of adding dichloromethane to the reactant and dissolving the same. This is a process of adding dichloromethane and dissolving the same in order to remove the solvent and effectively remove the remaining products.

In the dissolving (S50), it is preferable that 150 to 250 parts by weight of dichloromethane, more preferably, 200 parts by weight of dichloromethane is added to the 100 parts by weight of the first organic solvent. When the dichloromethane is less than 150 parts by weight, there is a problem that it is difficult to sufficiently dissolve the product, and when the dichloromethane exceeds 250 parts by weight, the excessive volume makes it difficult to remove the dichloromethane again later on, and is also uneconomical.

Next, the filtering (S60) is a step of filtering the reactant by passing silica and activated carbon through the reactant. This is a filtering process of further removing impurities included in the reactant which has gone through the dissolving (S50).

Since the reactant which has gone through dissolving (S50) is in a solution type, the impurities can be effectively removed as silica and activated carbon sequentially pass through the reactant and the impurities are attached to the silica and activated carbon.

Herein, it is preferable that 0.5 to 2 parts by weight of activated carbon is added to the 100 parts by weight of the first organic solvent, since that is when the filtration rate is the highest.

In addition, in the filtering (S60), the preferable filtering time is 4 to 8 hours, more preferably 5.5 to 6.5 hours. When the filtering time is less than 4 hours, the impurities cannot be filtered sufficiently, and when the filtering time exceeds 8 hours, it is not economical.

Lastly, the purifying (S70) is a step of removing the dichloromethane in the distillation under reduced pressure method and producing the purified 5-chloromethyl-2-furfural. This is a process of removing the dichloromethane added in the dissolving (S50) and consequently producing high purity 5-chloromethyl-2-furfural.

As in the separating or removing (S40), it is effective to remove chloromethane by distilling the chloromethane under a reduced pressure. Through this, it is possible to effectively remove only chloromethane without removing or damaging the final product, 5-chloromethyl-2-furfural.

The chemical structure of 5-chloromethyl-2-furfural obtained by the present disclosure is as in the following chemical formula 2:

[Chemical formula 2]

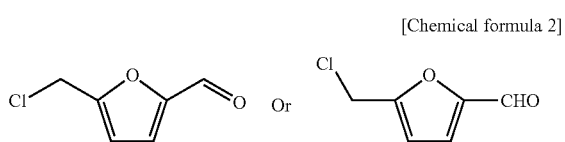 [SMILES: O=Cc1ccc(CCl)o1 ; O=Cc1ccc(CCl)o1]

5-chloromethyl-2-furfural is a precursor material of 5-Ethoxymethyl-2-furfural (EMF) and 2,5-Dimethylfuran (DMF), a precursor material of 2,5-Furan dicarboxylic acid (FDCA) known as an alternative material to the conventional Terephthalic acid (TPA) which is a petrochemical alternative compound, and can also be converted into Levulinic acid which is another platform compound, through diformylation reaction. Thus, 5-chloromethyl-2-furfural is a useful material which can be effectively used in various areas.

In addition, the conversion reaction of the method of producing 5-chloromethyl-2-furfural from galactan derived from seaweed on a two component phase, that is, the process of obtaining 5-chloromethyl-2-furfural which is the object material by means of a single process under the acid catalyst conversion condition without additional metal catalyst on a two component phase of dilute hydrochloric acid and halogen organic solvent using agarose which is the representative starting material is briefly shown in the reaction formula 1 below.

[Reaction formula 1]

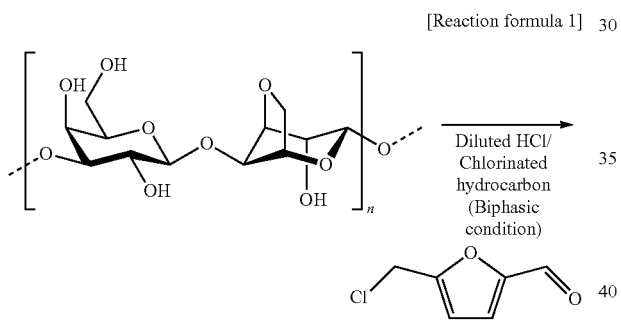

EXEMPLARY EMBODIMENTS

Hereinbelow is explanation on the acid catalyst composition for producing 5-chloromethyl-2-furfural from galactan derived from seaweed and experiment results for proving the excellence of a method for producing 5-chloromethyl-2-furfural from galactan derived from seaweed on a two component phase using the acid catalyst composition.

Production yields of 5-chloromethyl-2-furfural were compared based on exemplary embodiments 1 to 4 and comparative embodiments 1 to 2 where the method of the present disclosure was applied to cellulose.

Exemplary Embodiment 1

10 g of Agarose, 50 mL of 1,1,2-trichloroethane 50 mL, 25 mL of thick hydrochloric acid, and 25 mL of distilled water were put into a 1 L reactor, a screw cap was closed, and then stirred. The temperature was gradually raised up to 90° C., and after heating, the mixture was stirred by 200 rpm, and the reaction was proceeded for 1 hour. Herein, in 30 minutes after starting the reaction, the reaction solution turned from light yellow to dark brown. After finishing the reaction, the reaction solution was cooled to room temperature, 50 mL of distilled water and 50 mL of 1,2,3-trichloroethane were added, and then moved to a separating funnel to separate the dilute hydrocholoric acid layer and organic solvent layer, the solvent of the organic solvent layer was distilled under reduced pressure and then removed. The remaining product after removing the solvent was melted in dicholoromethane (about 100 mL), and then silica was passed through, and then 1 g of activated carbon was put in and then left for 6 hours. Finally, the activated carbon was filtered, dichloromethane was distilled under reduced pressure, and thus 3.84 g of 5-chloromethyl-2-furfural (CMF) was obtained.

Exemplary Embodiment 2

Using 3 Times of Organic Solvent 10 g of Agarose, 150 mL of 1,1,2-trichloroethane 50 mL, 25 mL of thick hydrochloric acid, and 25 mL of distilled water were put into a 1 L reactor, and a conversion reaction and a workup were performed in the same method as exemplary embodiment 1, and thus 4.32 g of CMF was obtained.

Exemplary Embodiment 3

Repeatedly Using Organic Solvent 3 Times 10 g of Agarose, 50 mL of 1,1,2-trichloroethane, 25 mL of thick hydrochloric acid, and 25 mL of distilled water were put into a 1 L reactor, and then a conversion reaction was performed in the same method as exemplary embodiment 1. After finishing the reaction, the organic solvent layer was separated by means of a separating funnel without any diluting process, and dilute hydrochloric acid layer was moved to the reactor again, and 50 mL of 1,2,3-trichloroethane was added, and additional conversion reactions were performed two more times. Organic solvent layers separated through each conversion reaction were collected, and a workup was performed in the same method as exemplary embodiment 1, and thus 3.40 g of CMF was obtained.

Exemplary Embodiment 4

Using 20% of Agarose 20 g of Agarose, 50 mL of 1,1,2-trichloroethane, 25 mL of thick hydrochloric acid, and 25 mL of distilled water were put into a 1 L reactor, and then a conversion reaction was performed in the same method as exemplary embodiment 1, and thus 6.28 g of CMF was obtained.

Comparative Embodiment 1

Using Cellulose Instead of Agarose 10 g of cellulose, 50 mL of 1,1,2-trichloromethane, 25 mL of thick hydrochloric acid, and 25 mL of distilled water were put into a 1 L glass, and then a conversion reaction and a workup were performed in the same method as exemplary embodiment 1, and thus less than 100 mg of CMF was obtained.

Comparative Embodiment 2

Using Small Amount of Agarose (1%, Wt/V)

1 g of agarose, 50 mL of 1,1,2-trichloroethane, 25 mL of thick hydrochloric acid, and 25 mL of distilled water were put into a 1 L reactor, and a conversion reaction and a workup were performed in the same method as exemplary embodiment 1, and thus 340 mg of CMF was obtained.

The results of the above experiments are shown in <Table 1>

TABLE 1

| | Exemplary embodiment 1 | Exemplary embodiment 2 | Exemplary embodiment 3 | Exemplary embodiment 4 | Comparative embodiment 1 | Comparative embodiment 2 |
|---|---|---|---|---|---|---|
| Amount of CMR produced | 3.84 g | 4.32 g | 3.40 g | 6.28 g | Less than 100 mg | 340 mg |

As shown in the above <Table 1>, in the cases of exemplary embodiments 1 to 4 of the present disclosure, the amounts of the final product, that is 5-chloromethyl-2-furfural, are more than 10 times that of comparative examples 1 and 2.

Therefore, one can see that the yield of the producing method of the present disclosure is far more excellent that conventional methods.

Figure 2:
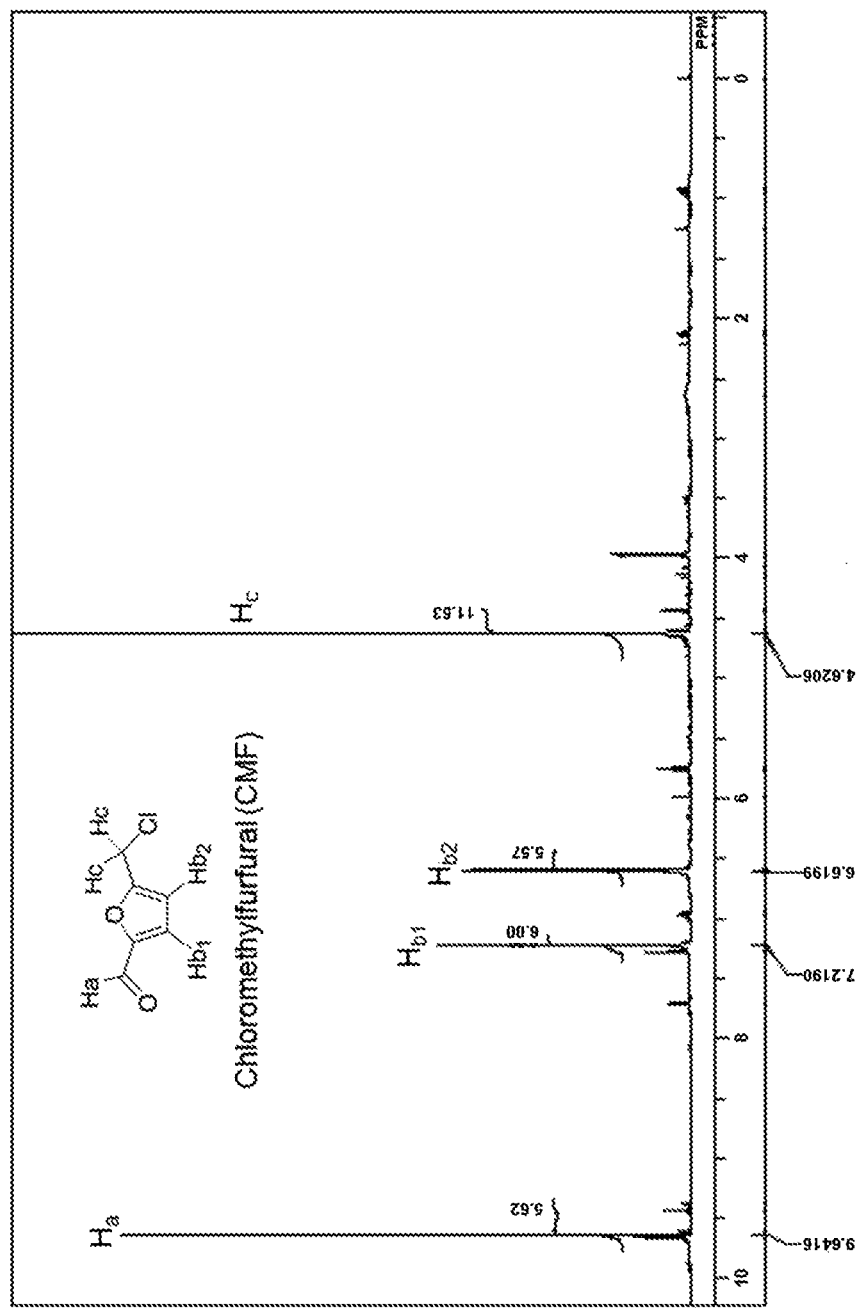
FIG. 2 is a graph measured by the nuclear magnetic resonance (NMR) method of 5-chloromethyl-2-furfural produced by the method for producing 5-chloromethyl-2-furfural from galactan derived from seaweed on a two component phase according to the present disclosure.
Figure 3:
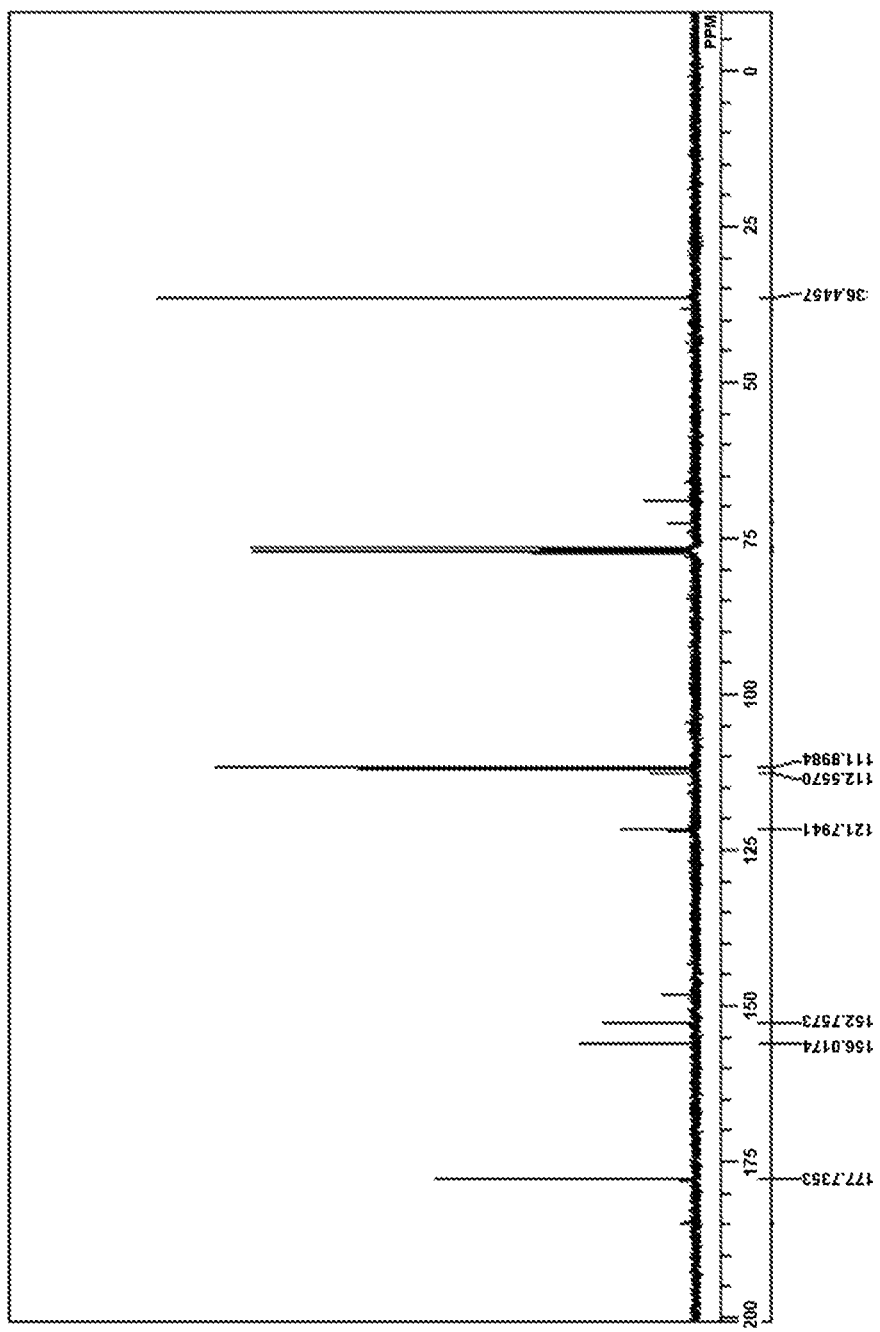
FIG. 3 is a graph measured by the nuclear magnetic resonance (NMR) method of 5-chloromethyl-2-furfural produced by the method for producing 5-chloromethyl-2-furfural from galactan derived from seaweed on a two component phase according to the present disclosure.

In addition, graphs of the products obtained through exemplary embodiment 1 of the present invention confirmed through the nuclear magnetic resonance (NMR) method are shown in FIGS. 2 and 3. Through these graphs, one can see that 5-chloromethyl-2-furfural is clearly generated from the present disclosure.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

INDUSTRIAL USABILITY

The present disclosure relates to an acid catalyst composition for producing 5-chloromethyl-2-furfural from galactan derived from seaweed which could significantly reduce processing costs and a method for producing 5-chloromethyl-2-furfural from galactan derived from seaweed on a two component phase using the acid catalyst composition, in a single process, by using dilute hydrochloric acid and organic solvent under optimal reaction conditions, and is thus industrially feasible.

What is claimed is:

1. A method for producing 5-chloromethyl-2-furfural from galactan derived from seaweed in two-component phase, the method comprising: mixing the galactan, a first organic solvent and dilute hydrochloric acid to produce a mixture; and reacting the mixture by heating to produce a reactant.

2. The method according to claim 1, further comprising: adding distilled water and a second organic solvent to the reactant; removing the first and the second organic solvent from the reactant; dissolving dichloromethane in the reactant by adding dichloromethane to the reactant; filtering the reactant; and purifying the reactant by removing the dichloromethane to produce purified 5-chloromethyl-2-furfural.

3. The method according to claim 1, wherein in the mixing, the dilute hydrochloric acid is 30 to 200 parts by weight of 100 parts by weight of the first organic solvent.

4. The method according to claim 1, wherein in the mixing, the first organic solvent is halogenated hydrocarbon solvent, and the halogenated hydrocarbon solvent is at least one of Dichloromethane, Chloroform, 1,2-Dichloroethane or 1,1,2-Trichloroethane.

5. The method according to claim 1, wherein in the mixing, the galactan is 10 g to 300 g in 1 L of dilute hydrochloric acid.

6. The method according to claim 1, wherein in the reacting, a reacting temperature is 50 to 200° C.

7. The method according to claim 1, wherein in the reacting, a reaction is made by stirring the mixture, and a stirring speed is 100 to 400 RPM.

8. The method according to claim 2, wherein the second organic solvent is 80 to 120 parts by weight, and the distilled water is 60 to 150 parts by weight of 100 parts by weight of the first organic solvent.

9. The method according to claim 2, wherein after the distilled water and the first organic solvent are added, the reactant is separated into a dilute hydrochloric acid layer and an organic solvent layer.

10. The method according to claim 2, wherein the dichloromethane is 150 to 250 parts by weight of 100 parts by weight of the first organic solvent.

11. The method according to claim 2, wherein a filtering time is 4 to 8 hours.

12. The method according to claim 2, wherein steps of removing and purifying are carried out by distillation under reduced pressure.

13. The method according to claim 2, wherein the filtering is carried out by passing the reactant through silica and activated carbon.

14. The method according to claim 1, wherein the organic solvent is halogenated hydrocarbon solvent.

* * * * *

UNITED STATES PATENT AND TRADEMARK OFFICE
CERTIFICATE OF CORRECTION

| | | |
|---|---|---|
| PATENT NO. | : 8,871,958 B2 | Page 1 of 1 |
| APPLICATION NO. | : 13/985019 | |
| DATED | : October 28, 2014 | |
| INVENTOR(S) | : Jin-Ku Cho et al. | |

It is certified that error appears in the above-identified patent and that said Letters Patent is hereby corrected as shown below:

In the specification

Col. 2, Line 31: delete "hus" and insert --Thus--.

Signed and Sealed this
Thirtieth Day of June, 2015

Michelle K. Lee
*Director of the United States Patent and Trademark Office*